(12) United States Patent
Borell

(10) Patent No.: US 6,190,340 B1
(45) Date of Patent: Feb. 20, 2001

(54) ARM, SHOULDER, AND BACK SUPPORT

(75) Inventor: Jan Borell, Hagerstown, MD (US)

(73) Assignee: Phillip and Joanne Borell, Wilson, KS (US)

(*) Notice: Under 35 U.S.C. 154(b), the term of this patent shall be extended for 0 days.

(21) Appl. No.: 09/172,123

(22) Filed: Oct. 14, 1998

(51) Int. Cl.⁷ .................................. A61F 5/00; A61F 5/02
(52) U.S. Cl. .................................. 602/4; 602/19; 602/20; 2/44; 2/45
(58) Field of Search .................................. 602/4, 5, 19, 20, 602/60–62; 473/207, 212, 215, 216; 2/44, 45, 305, 310, 311, 336, 341

(56) References Cited

U.S. PATENT DOCUMENTS

| 2,460,589 |   | 2/1949  | Lewis.                  |        |
|-----------|---|---------|-------------------------|--------|
| 2,560,243 | * | 7/1951  | Peterson                | 602/4  |
| 2,616,419 |   | 11/1952 | Karfiol.                |        |
| 2,796,862 |   | 6/1957  | Borntraeger.            |        |
| 3,108,589 |   | 10/1963 | Staggs.                 |        |
| 3,559,640 | * | 2/1971  | Beckett                 | 602/4  |
| 3,897,776 | * | 8/1975  | Gaylord, Jr.            | 2/44   |
| 4,337,938 |   | 7/1982  | Rodrigues.              |        |
| 4,570,619 | * | 2/1986  | Gamm                    | 2/45   |
| 4,751,923 |   | 6/1988  | Marino.                 |        |
| 4,815,639 |   | 3/1989  | Lehman.                 |        |
| 5,086,762 |   | 2/1992  | Chee.                   |        |
| 5,681,268 |   | 10/1997 | Rodman.                 |        |

FOREIGN PATENT DOCUMENTS

| 2585-561  | 2/1987 | (FR). |
| 565932    | 5/1944 | (GB). |
| 1393 418  | 5/1988 | (SU). |

* cited by examiner

Primary Examiner—Kim M. Lewis
(74) Attorney, Agent, or Firm—Michael L. Greenberg; Greenberg & Lieberman Law Offices

(57) ABSTRACT

A harness that fully supports the user's back, shoulders, and arms while working in a seated position. The harness provides support without restricting the user's freedom of movement. It is fully adjustable and conforms to a wide variety of user body types. Finally, it provides a safe, comfortable, and economic means of supporting the user's back, arms, and shoulders, allowing them to work more comfortably and possibly more efficiently.

7 Claims, 1 Drawing Sheet

ARM, SHOULDER, AND BACK SUPPORT

Priority is claimed to Document Disclosure No. 429,248 filed on Jan. 27, 1998, in the name of Jan N. Borell entitled "4-arms."

FIELD OF THE INVENTION

The present invention relates generally to an arm and shoulder support, and more specifically to a support harness which has straps that align the user's arms, shoulders, and spine in a more comfortable position while working in a seated position.

BACKGROUND OF THE INVENTION

People who type or work with their hands, while seated for extended time periods, often experience pain due to poor arm, back, and/or shoulder posture. For optimum comfort, a user's shoulders should both be held back equal distances from the user's chest to positions that straightly align the user's spine. The straightness of the user's spine is measured with respect to the user's neck while the user holds his or her neck straight and head up.

Even people who stand for extended periods of time suffer from poor posture, as they oftentimes slouch and stand with their back shifted to the side.

Several harnesses, slings, and supports have been developed to control posture by means of partially or completely immobilizing the user's shoulders, arm(s) and/or back. None of these devices control the user's back and shoulder posture, while at the same time providing comfortable support to the users' arms, without overly restricting the users' freedom of movement. Moreover, there exists no portable means of controlling the posture of a person's shoulders, arms, and back, for the purpose of reducing or preventing pain, while a person works with his or her hands in a seated position for an extended time period.

There are many ways to control a person's back, shoulder, and arm posture, but they facilitate only slight freedom of movement. The related art shows devices designed to support and restrict the movement of only one of the user's arms, such as U.S. Pat. No. 3,108,589, issued to Calvin H. Staggs on Oct. 29, 1963, U.S. Pat. No. 2,460,589, issued to A. V. Lewis on Feb. 1, 1949, and U.S. Pat. No. 2,616,419, issued to G. J. Karfiol on Nov. 4, 1952. Thus, the related art control the positioning of only one shoulder and one arm of the user, making it impossible to align and hold the user's spine straight. To set and maintain straight alignment of the user's spine, an invention must control the positions of both of the user's shoulders and arms.

U.S. Pat. No. 4,751,923, issued to Marino on Jun. 21, 1988, is another single arm support device, but it offers the additional feature of an adjustable strap for comfort and support of one shoulder. U.S. Pat. No. 2,796,862, issued to J. Borntraeger on Jun. 25, 1957, features cross straps which fasten to the user's waist belt to provide back support, but like all of the previously described prior art, this invention provides support for only one arm and one shoulder.

Many times, work such as typing is performed using two hands, and support for both arms and both shoulders is needed to work comfortably for an extended time period. Also, freedom of movement of one or both arms is needed to work comfortably and efficiently. U.S. Pat. No. 4,815,639, issued to Lehman on Oct. 8, 1987, facilitates more freedom of movement through the use of a single strap positioned across the middle of the user's chest. But, like all of the above-mentioned devices of the prior art, Lehman's invention supports only one of the user's arms. Additionally, Lehman's invention provides no back or shoulder support.

Foreign Patent No. GB 565,932, issued to Malby and Sons in December 1944, and Foreign Patent No. SU 1393-418-A issued to Mosc Eltrn Eng Inst on May 7, 1988, offer shoulder support and support for both of the user's arms. However, both of these inventions require attachment to devices rather than just to the user alone. Malby and Sons' device is designed to attach to the roof of a motor vehicle to support the arms and shoulders of a driver. Mosc Eltrn Eng Inst's device attaches to a work station where a user is seated, and it supports the user's arms while working at the work station. Neither of these inventions is portable for use in work areas other than those in which the supports are fixed. Further, neither of these inventions provide back support for users.

U.S. Pat. No. 5,681,268 issued to Stanley L. Rodman on Feb. 26, 1996, and U.S. Pat. No. 2,560,243, issued to M. C. Peterson on Jul. 10, 1951, provide support for both of the user's arms and provide back support for users. Additionally, both of these inventions are portable. But, both of these inventions restrict the freedom of movement of the user's arms, restricting the types of activities that the user is capable of performing. Further, Rodman's device has a fixed rigid shape which neither facilitates the adjustment of the back support nor the adjustment of the user's shoulder positions.

Foreign Patent No. FR 2585-561-A issued to Berrehail on Feb. 6, 1987, facilitates adjustment of the user's shoulder supports and back supports, but rigidly supports the user's arms in fixed positions. This arm support restricts the user's freedom of movement and limits the type of tasks the user is capable of performing. Further, this invention is complicated requiring the user to inefficiently put on and adjust many different parts for every each time the user wears the support.

U.S. Pat. No. 4,337,938, filed by Rodrigues on Mar. 6, 1981, provides a simple means of supporting the user's arms and shoulders, but this invention does not provide any back support.

Finally, U.S. Pat. No. 5,086,762, issued to Chee on Mar. 15, 1991, provides good support for a user's shoulders, elbows, and wrists while facilitating freedom of movement to allow users to perform a wide range of tasks. This invention utilizes a multiple straps which are fully adjustable. However, despite the fact that the user's arms and shoulders are fully supports, this invention provides no back support and users may experience back pain.

Therefore, a need has been established for a novel apparatus for supporting a person's back, shoulders, and arms while working in a seated position for extended time periods, by means of a support harness with adjustable straps.

It is an object of the present invention to provide an arm and shoulder support for a person's arms, shoulders, and back.

It is another object of the present invention to provide an arm and shoulder support which is portable.

It is also an object of the present invention to provide an arm and shoulder support which is a harness.

It is additionally an object of the present invention to provide an arm and shoulder support capable of being used in a multitude of different work environments.

It is another object of the present invention to provide an arm and shoulder support that does not restrict the user's freedom of arm movement.

It is yet another object of the present invention to provide an arm and shoulder support fully adjustable so that it is capable of being worn by a wide range of users.

It is a further object of the present invention to provide an arm and shoulder support which provides back support.

It is another object of the present invention to provide an arm and shoulder support that is easy to adjust.

It is also an object of the present invention to provide an arm and shoulder support which does not require adjustment after setting the initial strap positions.

It is another object of the present invention to provide an arm and shoulder support which is a single harness capable of supporting a user's arms, shoulders, and back.

SUMMARY OF THE INVENTION

The present invention is a support harness to provide comfort to users who work for extended time periods while seated or standing. The present invention simultaneously provides support to the user's arms, shoulders, and back, while not restricting freedom of arm movement.

The present invention incorporates several fully adjustable straps on a single harness allowing a wide range of users to select and set the shoulder, arm, and back support positions. Once the support positions are set, the user need not readjust the harness straps before the next use after removal.

The present invention incorporates two sets of straps across the back which provide a new way of supporting the user's back while maintaining good shoulder and arm posture. Further, the present invention provides arm supports that allow the user to have freedom to move his or her arms from side to side while the user's arms are fully supported at a fixed elbow bend angle.

After initial adjustment by the user, this invention automatically aligns the spine, arms, and shoulders with respect to one another, allowing users to work comfortably for long time periods while seated or standing.

DETAILED DESCRIPTION OF THE PREFERRED EMBODIMENT(S)

Figure 1:
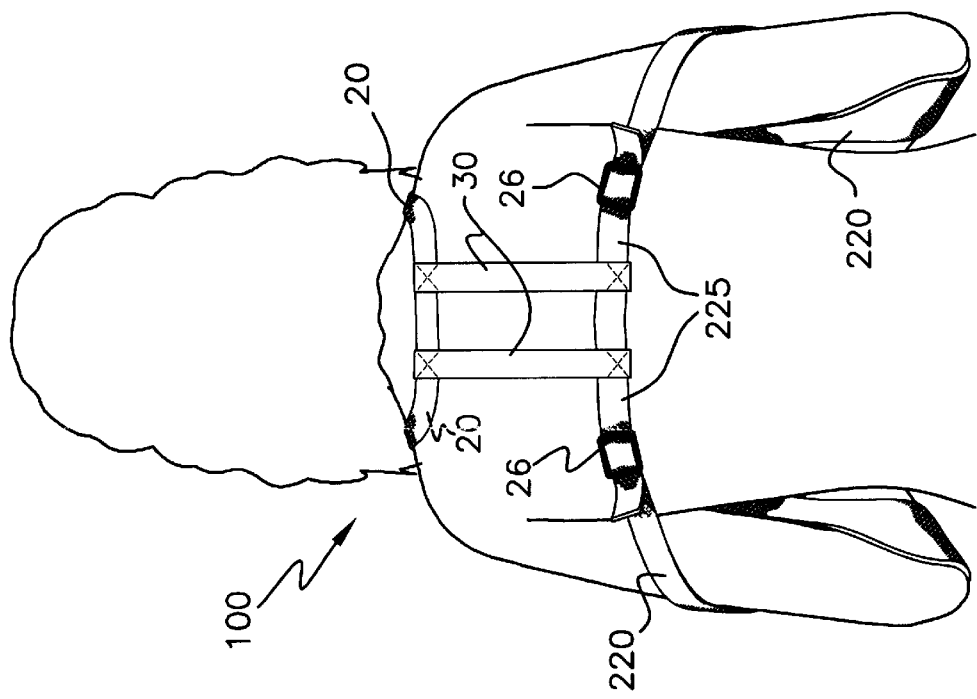
FIG. 1 is a front view of the present invention showing the arm support on a user.

The present invention incorporates several features into an arm, shoulder, and back support for better overall effectiveness. FIG. 1 shows how the harness (100) fits around the user's neck, over the user's shoulders, and under the user's elbows. This support configuration fully supports a user's arms, shoulders, and back, while the user works in a seated position.

Two upper straps (20) are formed from a single strip of material. The upper straps (20) terminate at adjustment buckles (25) similar to buckles commonly found on backpacks. The strip of material forming the upper straps (20) is sized to loop around the user's neck and allow the ventral adjustment buckles (25) to rest against the user's chest. The ventral adjustment buckles (25) rest approximately half way between the user's waist and shoulders, but closer to the shoulders. The adjustment buckles (25) facilitate ample adjustment of the harness (100) to allow a variety of user's to comfortably wear the same size harness (100).

Figure 2:
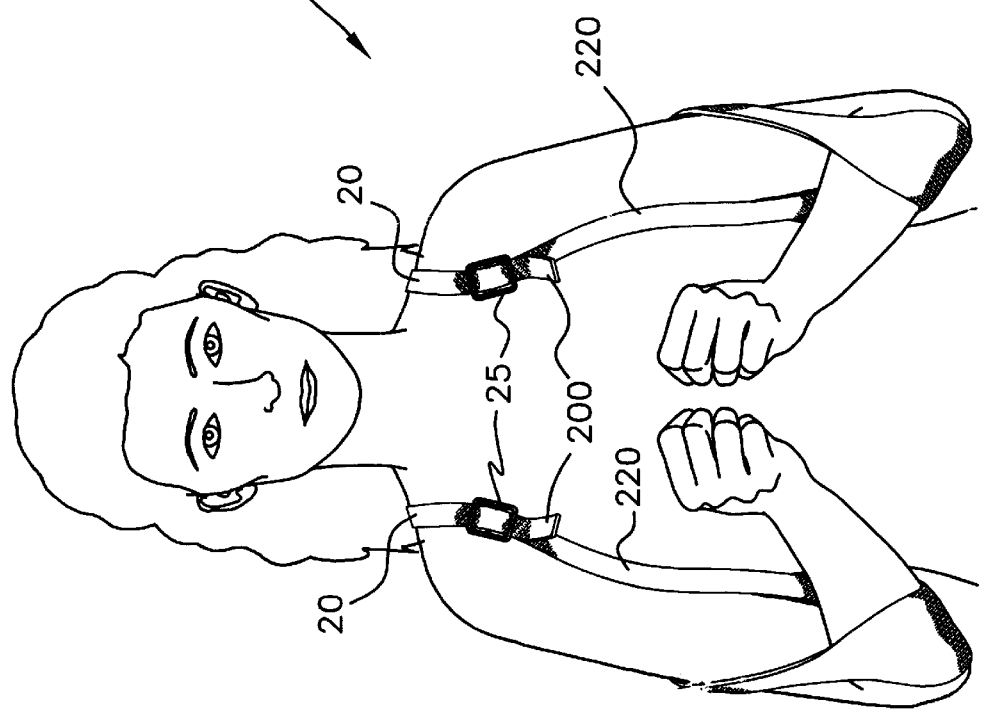
FIG. 2 is a rear view of the present invention showing the dual cross strap back support on a user.

Two lower straps (220) are formed from a single strip of material that loops around the back of the user, as shown in FIG. 2. The strip of material forming the lower straps (220) is joined to a piece of material forming mid straps (225) by dorsal adjustment buckles (26) similar to buckles commonly found on backpacks. Mid straps (225) fixedly connect to spacer straps (30) which are fixedly connected to upper straps (20). Thus, via dorsal adjustment buckles (26) and spacer straps (30), the strip of material forming the upper straps (20) at the dorsal end of the harness (100) connects to the lower straps (220).

In the preferred embodiment of the present invention, spacer straps (30) are sewn to the piece of material forming the upper straps (20) and the piece of material forming the lower straps (220). The spacer straps (30) are sized to comfortably position the pieces of material forming the upper straps (20) and lower straps (220). The spacer straps (30) hold the material forming upper straps (20) away from the user's neck while comfortably positioning the lower straps (220) across the user's back.

The strip of material forming the lower straps (220) is sized to extend across the users back, across the user's lower arms and forearms, under the user's elbows, and up to the ventral adjustment buckles (25). The lower straps (220) are sized long enough to fit onto the user as described above, with the ends (200) of the lower straps (220) inserted into the ventral adjustment buckles (25). Sufficient lower strap (220) reserve length exists to allow for adjustment of the harness (100) to accommodate a wide range of sizes of users.

As shown in FIG. 2, dorsal adjustment buckles (26) are provided for lower straps (220) to connect to mid straps (225). Dorsal adjustment buckles (26) are not required in the present invention, but they do permit the harness (100) to have further custom adjustments depending upon the size and shape of the user's torso. In an alternative embodiment, not shown, dorsal adjustment straps (26) and mid straps (225) are absent such that lower straps (220) extend to spacer straps (30) directly. In such an alternative embodiment, the present invention is simpler, but less adjustable.

In another alternative embodiment, the lower straps (220) are interrupted as they pass under each forearm. A soft section (221) is inserted against or in place of the lower straps (220) at the point where said lower straps engage the lower forearm to prevent the lower straps (220) from applying undue pressure to the forearms in this particular region. In all embodiments of the present invention, support and pressure are applied by lower straps (220) and upper straps (20).

In short, the present invention provides full support of the user's back, arms, and shoulders. The upper straps (20) loop around the user's neck, over the shoulders, and join the lower straps (220). The harness' (100) configuration holds the user's shoulders in a rearward position, and automatically aligns the user's back.

It is desirable to not employ mid straps (225) and dorsal adjustment buckles (26) in an embodiment of the present invention because the spacer straps (30) establish a fixed distance between the upper straps (20) and the lower straps (220) at the dorsal side of the harness (100), as shown in FIG. 2. This assures that the harness (100) will fit the same way every time it is worn by the user. The combination of the upper straps (20), the lower straps (220), and the spacer straps (30) provides a wide surface area supporting the user's back. The harness (100) is made to comfortably conform to the body shape of a wide range of users.

The lower straps (220) loop around the user's lower arms, under the elbows, and around the forearms, providing full support of the user's arms. However, despite the fact that the harness (100) fully supports the user's arms, the harness (100) does not overly restrict the user's freedom of arm, or hand movement, as shown in FIG. 2. The harness supports the user's arms while allowing the user to easily extend, twist, raise, and rotate his or her hands and arms. Further, the harness (100) supports the user's back but does not restrict the user from bending over or twisting his or her back. Finally, despite the fact that the harness (100) fits around the user's neck, the harness (100) does not restrict the users head or neck movement.

By providing full support to the user's arms, back, and shoulders, the harness (100) reduces and possibly eliminates pain for users working in a seated position. This harness allows workers to work comfortably making them more efficient and potentially allowing them to work for longer time periods.

In the preferred embodiment, the harness (100) is made with cloth straps sewn together using thread. The adjustment buckles (25, 26) are made of plastic. Any suitable material may be substituted for the strap material including but not limited to nylon, leather, or plastic. The buckles can be metal, plastic, or any other suitable material.

It is to be understood that the present invention is not limited to the embodiments described above, but encompasses any and all embodiments within the scope of the following claims.

I claim:

1. An arm, back, and shoulder apparatus, comprising
   an upper strap adapted to pass across a person's upper back and adapted to apply pressure thereto;
   a lower strap, in communication with said upper strap, said lower strap adapted to pass under a person's lower arms, elbows, and forearms and adapted to apply pressure thereto; and
   at least one spacer strap, positioned between said upper strap and said lower strap;
   wherein said upper strap and said lower strap are adapted to support a person's arms while allowing a person to easily extend, twist, rise, and rotate its hands and arms.

2. The apparatus of claim 1, further comprising a mid strap connecting said spacer strap to a dorsal adjustment buckle.

3. The apparatus of claim 1, further comprising a ventral adjustment buckle connecting said upper strap to said lower strap.

4. The apparatus of claim 1, further comprising a soft section attached to said lower strap.

5. An arm, back, and shoulder apparatus, comprising
   two upper straps;
   two lower straps, in communication with said upper straps, wherein said upper straps and said lower straps are adapted to support a person's back, arms, and shoulders and are adapted to apply pressure thereto; and
   at least one spacer strap, positioned between said two upper straps and said two lower straps.

6. The apparatus as in claim 5, wherein said lower straps are adapted to wrap around the forearms of a person.

7. An arm, back, and shoulder apparatus, comprising
   a means for applying pressure to a person's upper back;
   a means for applying pressure to a person's lower arms, elbows, and forearms, in communication with said means for applying pressure to a person's upper back;
   at least one spacer strap, positioned between said means for applying pressure to a person's upper back and said means for applying pressure to a person's lower arms, elbows, and forearms;
   wherein a person's arms are free to move laterally; and
   wherein said means for applying pressure to a person's upper back and said means for applying pressure to a person's lower arms, elbows, forearms are adapted to support a person's arms while allowing a person to easily extend, twist, raise, and rotate its hands and arms.

* * * * *